United States Patent [19]

Westphal et al.

[11] Patent Number: 5,545,997
[45] Date of Patent: Aug. 13, 1996

[54] THERAPY TOMOGRAPH WITH HOMOGENEITY DEVICE

[75] Inventors: Michael Westphal, Offenbach; Günther Laukien, Rheinstetten, both of Germany

[73] Assignee: Bruker Analytische Messtechnik GmbH, Rheinstetten, Germany

[21] Appl. No.: 502,237

[22] Filed: Jul. 13, 1995

Related U.S. Application Data

[63] Continuation-in-part of Ser. No. 437,598, May 9, 1995, Pat. No. 5,485,088.

[30] Foreign Application Priority Data

May 13, 1994 [DE] Germany .......................... 44 16 907.8
Jul. 12, 1995 [DE] Germany ......................... 195 25 322.1

[51] Int. Cl.$^6$ ................................................. G01V 3/00
[52] U.S. Cl. ........................... 324/320; 324/319; 335/216
[58] Field of Search ..................................... 324/320, 319, 324/318, 300, 307; 128/653.5; 335/216, 296, 297; 505/844

[56] References Cited

U.S. PATENT DOCUMENTS 5,389,909   2/1995   Havens ..................................... 324/320
5,485,088   1/1996   Westphal et al. ....................... 324/320

FOREIGN PATENT DOCUMENTS

2262611   6/1993   United Kingdom .......... G01R 33/38

Primary Examiner—Louis M. Arana

[57] ABSTRACT

In an NMR tomograph with superconducting main field coil (10) and large transverse access opening a compensation of inhomogeneities of the static magnetic field without hindering the axial and transverse access to the investigational volume (V) can be effected by the following elements: ferromagnetic homogeneity elements (20) which are arranged on the surface of the room temperature bore on both sides of the transverse access opening; at least one or more (a number $p \geq 1$) superconducting correction coils ($C_1$ and $C_p$) which can be separately supplied with current and which are coaxial to the main field coil (10), whereby each correction coil ($C_1$ through $C_p$) comprises at least two partial coils ($C_{1i}$, $C_{1a}$ through $C_{pi}$, $C_{pa}$), whereby all partial coils of all correction coils ($C_1$ through $C_p$) are cylindrical coils coaxial to a common axis (z) having a diameter less than the inner diameter ($d_{a2}$) of the outer field coil (1a, 1b), whereby in each correction coil one partial coil ($C_{1i}$ through $C_{pi}$) has, in each case, as small a separation from the middle plane (E) as possible generally equal to the separation of the radially inner field current pair (2a, 2b) from the middle plane and whereby each correction pair has, in each case, at least one second partial coil ($C_{1a}$ through $C_{pa}$) with an oppositely directed current which has a larger axial separation from the middle plane (E) than the radially inner field coil pair (2a, 2b).

9 Claims, 4 Drawing Sheets

THERAPY TOMOGRAPH WITH HOMOGENEITY DEVICE

This application is a continuation-in-part of application Ser. No. 437,598 filed May 9, 1995 now U.S. Pat. No. 5,485,088.

BACKGROUND OF THE INVENTION

The invention concerns a nuclear magnetic resonance (NMR) tomograph with a superconducting main field coil for the production of a static, homogeneous magnetic field in an investigational volume of the magnetic resonance imaging system whose center coincides with the center of a coordinate origin of a cartesian x-, y-, z-coordinate system, having a pair of mutually similar outer field coils which are arranged on a common axis (z) at an axial separation ($g_1$) with respect to each other as well as a pair of inner likewise mutually similar field coils coaxial to the outer field coils, whereby both coils pairs are arranged symmetrically with respect to a central middle plane (E) which runs perpendicular to the common axis (z), whereby the axial separation ($g_1$) of the outer field coils assumes a value between ¼ and ¾, preferentially ½ of the inner diameter ($d_{a2}$) of the outer field coils, whereby the axial separation ($g_2$) of the inner field coils is slightly, e.g. up to 15%, different than the axial separation ($g_1$) of the outer field coils, whereby, during operation of the main field coil, the current flow direction in the inner field coils is oppositely directed to that in the outer field coils, with an axial room temperature bore extending in the direction of the homogeneous magnetic field and a transverse access opening extending transversely to the direction of the homogeneous magnetic field and having a device for the compensation of inhomogeneities in the static magnetic field.

An NMR tomograph of this kind is known the art, for example, from DE 39 07 927 A1.

The main field coil of the tomograph which is known in the art consists of a double Helmholtz-coil configuration with opposite current directions. An NMR tomography magnetic system of this type, having relatively small axial and radial dimensions as well as relatively low overall weight, facilitates a free access to the investigational volume from a plurality of different directions, whereby the configuration is also relatively insensitive to eddy currents which can occur during switching of the field gradients necessary for tomography. Transverse access openings to the investigational volume are particularly important since claustrophobia problems are strongly reduced or do not occur for the patient being examined in the tomograph. In addition, a plurality of therapeutic measures, for example surgery, in particular microsurgery or irradiation, which can be directly monitored and checked with a tomography apparatus, require as free an axial and transverse access to the patient as possible.

On the other hand, the NMR slice images which are created with a therapeutic tomograph of this type should have as high a resolution and as high a signal-to-noise ratio as possible. For this reason it is necessary for the static magnetic field produced by the main field coil in the investigational volume to have as high a homogeneity as possible.

A useful mathematical tool for the description of inhomogeneities in a region about the symmetry center of a magnetic field is given by the expansion of the field in spherical harmonics. In NMR tomographs only the axial, e.g. the z-components dominate. In general one has:

$$B_z = A_{00} + \sum_{n=1}^{\infty} r^n \sum_{m=0}^{n} P_{nm}(\cos\theta) [A_{nm}\cos m\phi + B_{nm}\sin m\phi]. \quad (1)$$

In ideal rotationally symmetric configurations all terms in the sum vanish which are associated with non-rotationally symmetric field components, e.g. all terms with m not equal to 0. In the usual notation these types of terms are designated "tesseral" whereas terms having m=0 are called "zonal".

Furthermore with a mirror-symmetric configuration all terms except those with amplitudes $A_{n0}$ having odd values of n vanish. In addition with coil configurations associated with the above cited DE 39 07 927 A1, all terms with n<8 vanish. The following expression then results for the homogeneous magnetic field in the z-direction:

$$B_z = A_{00} + \sum_{n \geq 8, \text{ odd}}^{\infty} A_{n0} r^n P_{n0}(\cos\theta). \quad (2)$$

In particular along the z-axis one has for the double Helmholtz-configuration with oppositely directed currents $$B_z = A_{00} + A_{80} z^8 + A_{10,0} z^{10} + \quad (3)$$

$A_{00}$ is the desired homogeneous field. The remaining terms represent field distortions which are unavoidable with this coil configuration even in the event of a perfect construction which at z- or r-values of 20 cm from the symmetry center have relative, e.g. relative to $A_{00}$, magnitudes of approximately 10 ppm. For smaller z- or r-values these distortions are generally much smaller due to the $z^n$-dependence ($n \geq 8$) so that, within a spherical volume about the symmetry center with a diameter of approximately 40 cm, only field distortions below 10 ppm occur and high quality NMR imaging methods are thereby possible.

Due to mechanical tolerances during the manufacture of the coil bodies as well as to the in principle helical instead of ideally rotationally symmetrical shape of the windings of the main field coil, one obtains deviations from this ideal behavior which can result in non-vanishing distortion amplitudes $A_{nm}$, $B_{nm}$ with n<8 and m≧0. In practice one must experimentally determine these distortion amplitudes through measurements and compensate for them with the assistance of superconducting or resistive auxiliary coils or with strategically and advantageously placed pieces of iron, for example in the bore of the magnet coil.

A compensation of this kind is known in the art as "shiming". For example, superconducting shim-coils are described in DE 35 11 303 A1. The utilization of ferromagnetic shim plates is known in the art from DE 17 64 564 A1.

With a therapeutic tomograph having sidewardly and axially open coil systems facilitating both an axial as well as a transverse access to the investigational volume, there is the additional difficulty compared to conventional tomographs that there is neither a bore for securing iron pieces nor another support body for attaching superconducting or resistive correction coils in the entire region of the sideward access opening. Substantial limitations therefore obtain for the placing of shim elements. Certain types of field distortions can therefore no longer be easily compensated for. The preferred locations in conventional systems for these types of shim elements, in the middle region near to the homogeneity volume, are located, in the described therapy systems, in the vicinity of the transverse access and therefore must remain free.

Furthermore it is necessary, with all superconducting correction coils, to prevent inductive coupling to the superconducting main field coil. Otherwise, for example, a time dependent drift of the homogeneous magnetic field produced by the main field coil would lead to a discharge of the correction coils.

It is therefore the purpose of the present invention to introduce an NMR tomograph of the above mentioned kind with which homogeneity of the magnetic field is facilitated without hindering the axial or transverse access to the investigational volume.

SUMMARY OF THE INVENTION

This purpose is achieved in accordance with the invention in that the device for compensation of static magnetic field inhomogeneities includes the following elements:

ferromagnetic homogeneity elements, preferentially plates, which are brought onto certain positions at the surface of the room temperature bore on both sides of the transverse access opening in such a fashion that at least one component of the tesseral field distortion of the type $A_{nm}$ with n=1 through 3, preferentially n=1 through 6, and m=1 through n are compensated, at least one or more (a number $p \geq 1$) superconducting correction coils ($C_1$ through $C_p$) which can be separately fed with current and which are arranged coaxially with respect to the main field coil, whereby each correction coil ($C_1$ through $C_p$) comprises at least two partial coils ($C_{1i}$, $C_{1a}$ through $C_{pi}$, $C_{pa}$) which have current flowing through them in opposite directions during operation, whereby all partial coils of all correction coils are cylindrical coils coaxial to the common axis (z) having a diameter which is less than the inner diameter ($d_{a2}$) of the outer field coils, whereby, in each correction coil ($C_1$ through $C_p$) a partial coil ($C_{1i}$ through $C_{pi}$) has, in each case, as small a separation with respect to the middle plane (E) as possible, which is generally equal to the separation of the radially inner field coil pair from the middle plane so that these partial coils extend in an axial region $g_2/2 \geq |z| \geq g_2/2+b$ and whereby each correction coil ($C_1$ through $C_p$) has, in each case, at least one second partial coil ($C_{1a}$ through $C_{pa}$) having opposite current flow direction, which has a larger axial separation from the middle plane (E) than the radially inner field coil pair.

The underlying realization of the invention is that, by introducing iron on the inner cylinder outside of the middle region where the sideward access openings are located, a simultaneous compensation of all tesseral and zonal distortion terms is not possible. However, a complete compensation of all tesseral terms alone to at least 6th order (n=1 through 6; m=1 through n) is possible. Thereby additional zonal distortion terms, in particular $A_{20}$, $A_{40}$, $A_{60}$, are produced which, however, can be kept relatively small. The solution-principle of the present invention is that all tesseral terms up to 6th order are compensated by means of ferromagnetic homogeneity elements on the inner cylinder of the room temperature bore outside of the middle region (access opening), whereas all remaining zonal distortion terms can be corrected through special superconducting correction coils which are accommodated along with the superconducting main field coil in a helium cryostat.

In an embodiment the winding numbers of all partial coils of a correction coil are chosen in such a fashion that the mutual inductance between the main field coil and the correction coil vanishes. In this manner a coupling between the main field coil and correction coils can be completely avoided. Therefore no discharge of the correction coils in the event of a possible drift of the main field coil takes place and the danger of destroying superconducting correction coils in the event of quench of a superconducting coil system is avoided.

In a further preferred embodiment all partial coils of the correction coils which are closest to the middle plane (E) have a larger inner diameter than the outer diameter $d_{i1}$ of the inner field coil pair. This leads to particularly high amplitudes for the produced correction field.

In another preferred embodiment one provides that, with at least one correction coil, the partial coil closer to the middle plane has a larger inner diameter and the partial coil more distant from the middle plane a smaller inner diameter.

With these measures particularly high correction field amplitudes can also be obtained.

Even higher produced correction field amplitudes are obtained in an improvement of this embodiment with which the inner diameter of the additional correction coil partial coil distant from the middle plane is approximately equal to the inner diameter $d_{i2}$ of the inner field coil.

In another preferred embodiment one provides that, in at least one correction coil, both partial coils have approximately the same inner diameter.

In an embodiment of the NMR tomograph in accordance with the invention which is compact and particularly simple to produce one provides that the correction coil partial coils closer to the middle plane are accommodated in a common coil support winding chamber together with the corresponding inner field coil and the correction coil partial coils distant from the middle plane are accommodated in an additional common coil support winding chamber.

In an embodiment of the NMR tomograph in accordance with the invention, the ferromagnetic homogeneity elements can be at least partially replaced by an additional system of superconducting correction coils in the form of saddle coils which are arranged generally at the radius of the inner field coil. In this fashion the conventional tedious experimental determination of the locations of the homogeneity elements is replaced by a simpler experimentation with the additional saddle coil correction currents.

Finally, in an alternate embodiment, the ferromagnetic homogeneity elements are permanent magnets. In this fashion the direction of the magnetization relative to the field direction can be fully chosen so that additional improved possibilities for compensation of field distortions are given.

With the NMR tomography system in accordance with the invention, additional room temperature shim systems can be provided to eliminate field distortions of the types $A_{10}$, $A_{11}$ and $B_{11}$ as well as $A_{20}$ can be provided. In this fashion an additional degree of freedom compared to a system having solely superconducting persistent current mode operated shim coils can be achieved.

In particular, field distortions of the type $A_{11}$ and $B_{11}$ can be compensated for by a weak DC portion in an x-, y-gradient coil system according to FIGS. 8, 9a and 9b of DE 42 30 145 A1 and the accompanying description the complete contents of which is herein incorporated by reference. Instead, additional shim coils can also be provided for which have a spatial construction corresponding to that of the gradient coils described in DE 42 30 145 A1.

A correction of field distortions of the type $A_{10}$ can be eliminated through a shielded z-gradient coil system in accordance with DE 42 30 145 A1 which realizes the features of claim 14 and 15 of the above mentioned laid open publication.

Finally, field interference from distortion terms of the type $A_{20}$ can be compensated by four air coils wound coaxially with respect to the z-axis which are positioned either at the inner wall of the room temperature bore or on the inner side of a transverse access opening.

Further advantages of the invention can be derived from the description and the accompanying drawing. The above mentioned features in accordance with the invention as well as those to be described below can be utilized individually or collectively in arbitrary combination. The embodiments shown and described are not to be considered as an exhaustive enumeration, rather have exemplary character only.

The invention is represented in the drawing and is described and explained with the assistance of concrete embodiments.

DESCRIPTION OF THE PREFERRED EMBODIMENT

Figure 1:
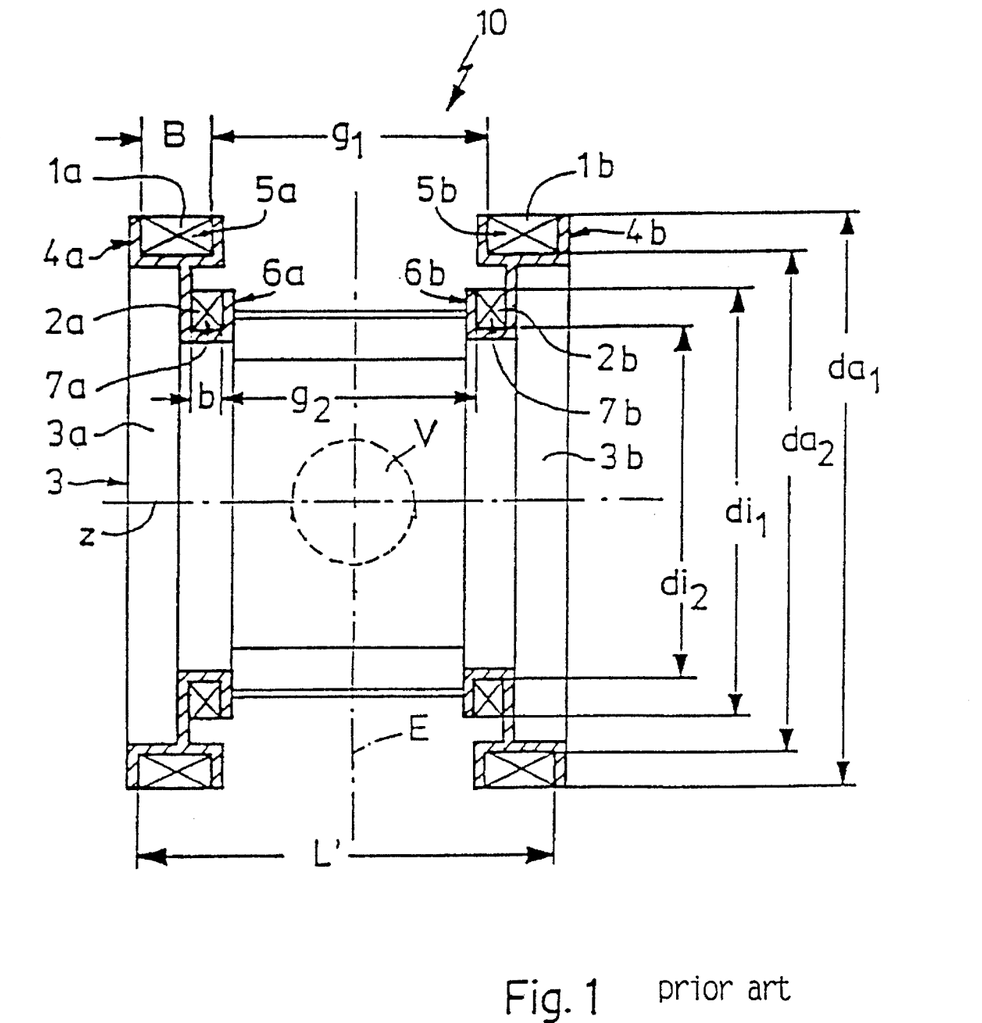
FIG. 1 shows a main field magnet system having transverse access according to prior art in a simplified schematic cut representation in a radial plane containing the central longitudinal axis z of the magnet system.

The main field coil system 10 represented in FIG. 1 includes an outer pair of windings or field coils 1a and 1b as well as an inner pair of windings or field coils 2a and 2b which run coaxially along a common central axis z and are generally symmetrically positioned relative to a central transverse middle plane E extending at right angles to the central axis. The outer windings 1a and 1b as well as the inner windings 2a and 2b are wound on a coil body labelled in its entirety with 3 comprising two support rings 3a and 3b which support the outer and inner windings 1a and 2a and 1b and 2b respectively each arranged on one side of the transverse middle plane E. These coil body 3 support rings 3a and 3b each have outwardly facing perpendicular mutually adjacent U-shape defining section arms 4a or 4b by means of which, in accordance to the representation of FIG. 1, the clearance width B in the axial direction as well as the radially measured depth $(d_{a1}-d_{a2})/2$ of the rectangular cross-sectional area of the winding chambers 5a or 5b spanned by the windings of the outer field coil 1a or 1b in as dense a packing as possible is defined, whereby $d_{a1}$ designates the outer diameter and $d_{a2}$ the inner diameter of the outer winding 1a or 1b.

Furthermore, the support rings 3a and 3b each have an inner profile defined by perpendicular mutually adjacent U-shape defining section arms 6a or 6b which, according the representation of FIG. 1, likewise open outwardly and by means of which the clearance width b in the axial direction as well as the radially measured depth $(d_{i1}-d_{i2})/2$ of the likewise rectangular cross sectional shape of the winding chambers 7a or 7b which is spanned by the windings in the inner field coils 2a or 2b in as dense a packing as possible is defined, whereby $d_{i1}$ designates the outer diameter and $d_{i2}$ the inner diameter of the inner winding 2a or 2b. The support rings 3a or 3b of both partial coil pairs are, for practical reasons, formed from separate partial rings $3a_1$ and $3a_2$ or $3b_1$ and $3b_2$ for acceptance of one winding 1a and 2a or 1b and 2b each. After winding the windings the partial rings are each assembled into one support ring 3a or 3b and securely connected to each other. The support rings 3a and 3b formed in this fashion are, for their part, securely connected to each other by means of longitudinal struts 8, whereby the axial separation of the support rings 3a and 3b can be adjusted in a manner not shown.

Figure 2:
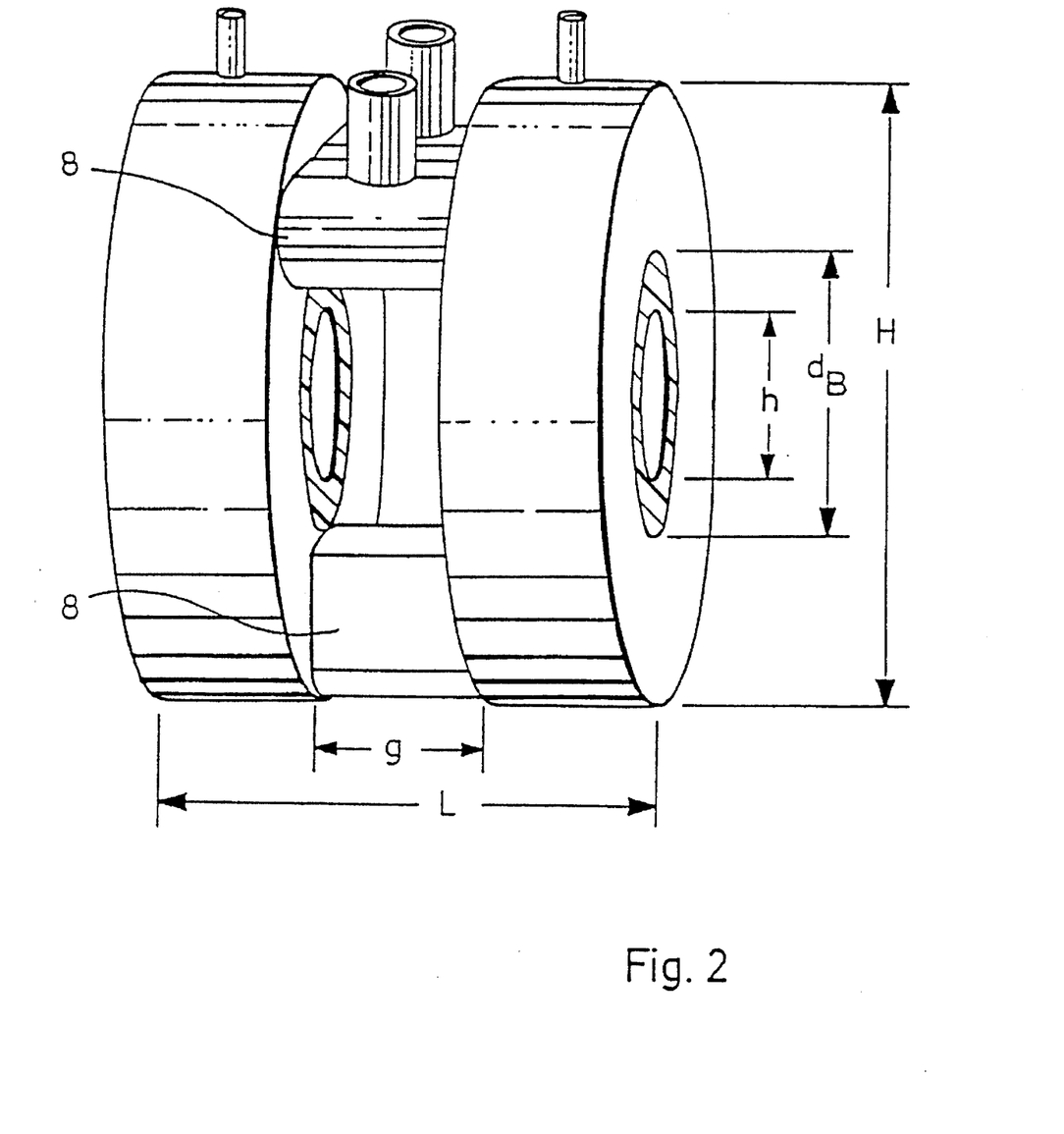
FIG. 2 shows a perspective overall view of the NMR tomography system in accordance with the invention with associated cryostats for a superconducting main field magnet coil.

In the preferred embodiment shown in FIG. 2, the coil body 3 includes three such longitudinal struts which are arranged symmetrically with respect to the longitudinal middle plane marked by the plane of the drawing and containing the central z axis of the magnet system 10 and thereby, as viewed along the perpendicular axis, can be grouped axially symmetrically about the axis at equal angular separations. The axial forces which the windings 1a, 1b and 2a, 2b exercise upon each other in the current flowing state of the magnet system are taken-up by the struts 8. The axial separation $g_1$, at which the outer windings 1a and 1b are arranged with respect to each other, can be varied in the magnet system 10 between ¼ and ¾ of the inner coil diameter $d_{a2}$ of the outer field coils 1a or 1b, whereby a preferred value of this separation $g_1$ is approximately half this inner coil diameter $d_{a2}$.

The axial separation $g_1$ at which both windings 1a and 1b of the outer coil pair can be separated from each other can assume a value between ¼ and ¾ of the inner diameter $d_{a2}$ of the outer coil pair 1a, 1b and, in a particular configuration of this coil pair, is approximately, e.g. within a deviation of ±10%, half as large as the inner coil diameter $d_{a2}$. In this fashion the center of gravity of the winding cross sections 1a and 1b (axially $(g_1+B)/2$, radially $(d_{a1}+d_{a2})/2$) are axially further separated than in a Helmholtz-configuration of the winding pair.

The inner coil pair 2a, 2b is smaller, with respect to its characteristic dimensioning—outer diameter $d_{i1}$ and inner diameter $d_{i2}$—than the outer coil pair 1a, 1b, whereby the magnitude of its winding density is equal to that of the outer coil pair. If necessary the winding densities can differ.

The axial separation $g_2$ of the inner winding 2a and 2b is, to a deviation of at most 15%, equal to the axial separation $g_1$ of the outer windings 1a and 1b and, in the special embodiment represented, is slightly smaller than the axial separation $g_1$ of the outer winding 1a and 1b, so that the axial clearance between the two windings 2a and 2b is similar to that between the two outer windings 1a and 1b.

The current flowing through the inner pair of winding 2a, 2b during operation of the magnet system 10 is, with regard to its direction, opposite to that flowing through the outer pair 1a, 1b so that the magnetic fields produced by the two winding pairs 1a, 1b and 2a, 2b are directed oppositely to each other, whereby the winding numbers of the outer winding 1a and 1b, assuming the same current strength in the windings 1a and 1b as well as in 2a and 2b, compared to the winding numbers of the inner windings 2a and 2b have a ratio of approximately 4/1, whereby this ratio can vary within a margin of ±20%.

Through a suitable choice of strength of the currents which flow through both winding pairs 1a, 1b and 2a, 2b, it is possible to produce a static magnetic field which is sufficiently homogeneous within the circular bordered investigational volume V indicated with dashed lines in FIG. 1 whose diameter is approximately 40 cm (field deviation 20 ppm).

In a preferred configuration of the magnet system 10 with superconducting magnet coils, the axial separation $g_1$ of the outer winding pairs 1a, 1b assumes a value of 887 mm and the axial width B of the winding chamber, 220 mm. The axial extension L' between the outer walls of the winding chambers 5a and 5b of the magnet system 10 assumes a value of 1327 mm. The inner diameter $d_{a2}$ of the outer winding chambers 5a and 5b assumes a value of 1818 mm and the outer diameter $d_{a1}$ of the outer windings 1a and 1b, 1997 mm. The winding density in the outer winding chambers 5a and 5b assumes a value of 18.40 windings/cm$^2$.

The axial separation of the winding chambers 7a and 7b of the inner winding pair 2a, 2b assumes a value of 881.5 mm, whereby the axial width b of these winding chambers 7a and 7b assumes a value of 39.2 mm in each case. The inner diameter $d_{i2}$ of the windings 2a and 2b has a value of 1400 mm, whereas the outer diameter $d_{i1}$ of the inner windings 2a and 2b has a value of 1507 mm. The winding density of the inner windings 2a and 2b is opposite to that of the outer windings 1a and 1b and has a value of −46.73 windings/cm$^2$. With the mentioned separation $g_2$ of the winding chambers 7a and 7b of the inner coil pair 2a and 2b, it is possible to construct a superconducting cryogenic magnet system with a usable intermediate volume z of 660 mm and a room temperature bore having a diameter of 1250 mm for the acceptance of gradient coils in accordance with the invention.

With a current strength of 157 A, a homogeneous magnetic field in the center of the magnet system 10 of 0.5 Tesla results.

The perspective overall view of an embodiment of the NMR measuring system in accordance with the invention of FIG. 2 shows, among other things, the overall height H of the apparatus which is determined by the outer diameter of the cryostat, the height h of the horizontal patient bore, the width g of the sideward access opening to the central investigational volume, and the length L of the entire apparatus.

Further details of the cryostat system superconducting main field magnet coil which is likewise shown in FIG. 2 are not discussed here. All superconducting coils are accommodated in the helium tank of the cryostat.

Figure 3:
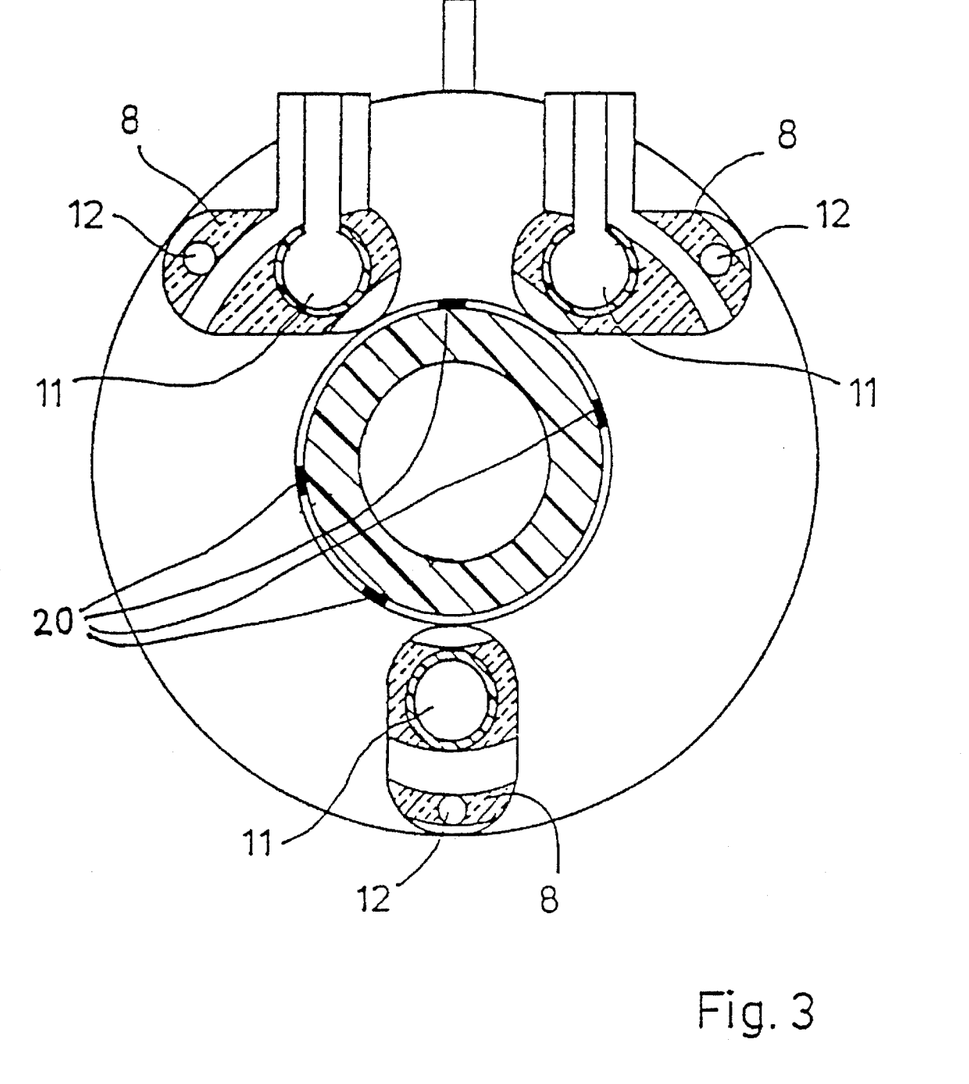
FIG. 3 shows a cut through the sideward access opening of the system represented in FIG. 2 with a view onto the patient bore of one of the two main coil halves and the shim plates introduced therein.

FIG. 3 shows a cut through the sideward access opening of the NMR tomograph which is perpendicular to the central z axis. Connecting pipes 11 between the two sides of the helium tank of the cryostat system containing the superconducting magnet coil as well connecting pipes 12 between the liquid nitrogen tanks surrounding the helium tanks are visible through the cut-open longitudinal struts 8. The conventional radiation shields are not shown. Ferromagnetic homogeneity elements 20 in the form of shim plates are distributed around the room temperature bore.

Figure 4:
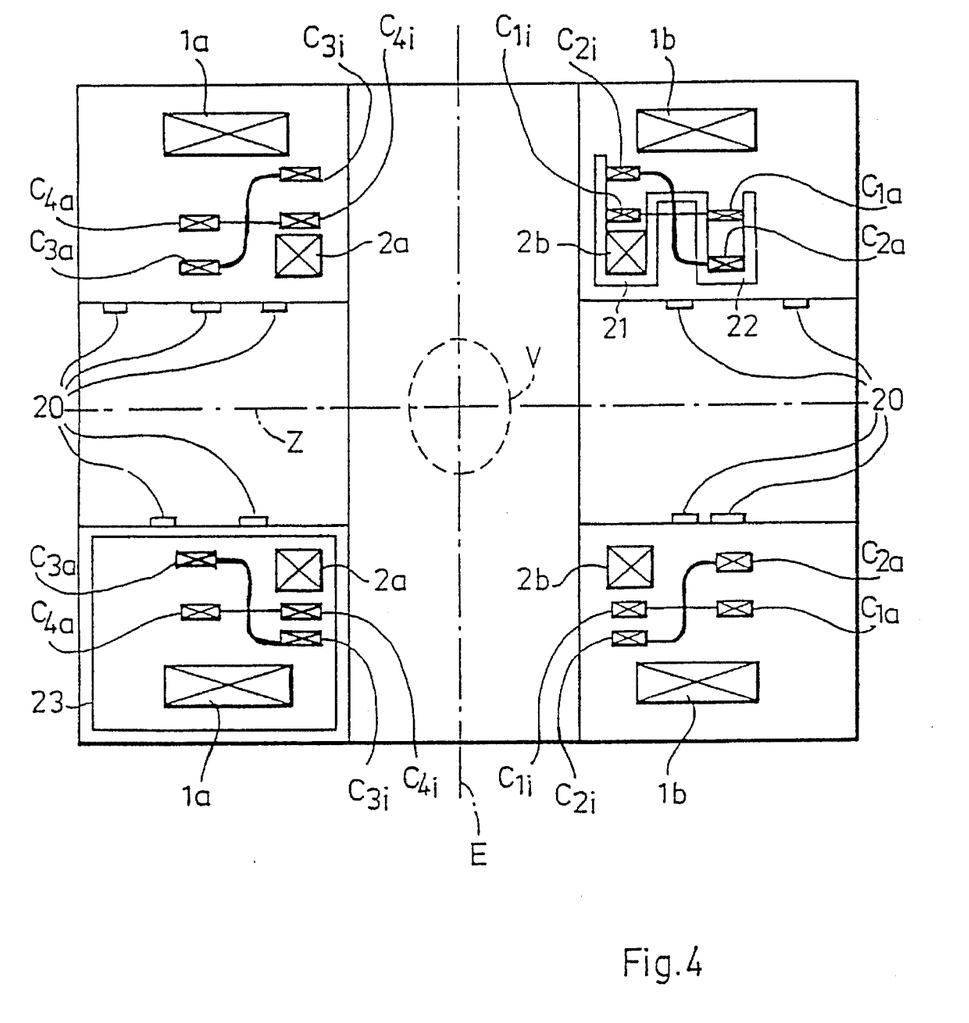
FIG. 4 shows a schematic cross sectional representation of the NMR tomography system in accordance with the invention in a radial plane containing the central longitudinal axis z of the magnet system.

FIG. 4 shows a schematic cross section through the NMR tomography system in accordance with the invention in a plane which contains the z axis. Outer field coils 1a and 1b as well as the inner field coils 2a and 2b on both sides of the middle plane E can be recognized. Four superconducting correction coils $C_1$ through $C_p$, which can be separately fed with current, are arranged symmetrically about the z axis radially within the outer field coils 1a and 1b. Each correction coil $C_1$ through $C_p$ comprises at least two partial coils $C_{1i}$, $C_{1a}$ through $C_{pi}$, $C_{pa}$ which are driven with oppositely directed currents during operation. Each correction coil $C_1$ through $C_p$ contains a partial coil $C_{1i}$ through $C_{pi}$ which has as small a separation as possible with respect to the middle plane E and which extends generally in an axial region $g_2/2 \geq |z| \geq g_2/2+b$. At least one second partial coil $C_{1a}$ through $C_{pa}$ of each correction coil $C_1$ through $C_p$ has, in contrast, a larger axial separation from the middle plane E than the radially inner field coil pair 2a or 2b.

A coil support is indicated in the right upper quadrant of the configuration schematically shown as a cross section in FIG. 4, which comprises a winding chamber 21 in which the partial coils $C_{1i}$ and $C_{2i}$ which are closer to the middle plane E are commonly accommodated together with the inner field coil 2b. The partial coils $C_{1a}$ and $C_{2a}$ which are located further from the middle plane E are mutually accommodated in an additional coil support winding chamber 22. Similar common winding chambers are also provided for the other four quadrants of the represented cross section but are not shown in the drawing of FIG. 4 for reasons of clarity.

A chamber 23 having liquid helium is represented in the lower left quadrant of the schematic cross sectional drawing in which the corresponding superconducting coil portions of the lower left quadrant are accommodated. The helium chamber is likewise not shown in the remaining quadrants of FIG. 4 for reasons of clarity.

The electrical switching of the partial coils can, in an embodiment not shown in the drawing, also be such that two coil parts of a particular correction coil are arranged on either side of the middle plane E.

Indicated in FIG. 4 on the inner side of the indicated room temperature bore at various locations along the z-axis are, finally, ferromagnetic homogeneity elements 20 which must not necessarily be distributed in a symmetric fashion relative to the plane E or the z-axis. The concrete locations for placing of the corresponding homogeneity elements 20 is individually experimentally determined for each NMR system in such a manner that the tesseral field distortions are largely eliminated.

Plates on the order of 50×40×0.3 mm$^3$ placed on the surface of the room temperature bores in both cryostat halves are preferred. As already mentioned the axial extension for the distribution of the ferromagnetic correction elements 20 usually lies in the range between $|z|=g/2$ and 1.4 g, whereby g is the width of the transverse access opening to the investigational volume V.

The mounting radius r for the correction elements 20 (=radius of the room temperature bore) typically assumes a value of approximately 1.8 $g \geq r \geq 2$ g.

The ferromagnetic correction elements 20 are arranged in such a fashion that only the tesseral distortion terms (m not equal to 0) as well as the odd zonal distortion terms (n odd, m=0) vanish. Due to the large separation of the iron pieces from the middle plane E, this iron distribution produces, in principle, additional zonal distortion terms $A_{20}$, $A_{40}$, $A_{60}$ which add to those produced by the main field coil of the same kind. The zonal distortion terms $A_{40}$ and $A_{60}$ can likewise be kept negligeably small. There are mathematical methods with which the amount of iron utilized can be minimized. The sign of the $A_{20}$ term is $A_{20}<0$.

A compensation of the remaining zonal distortion terms is effected in accordance with the invention with the assistance of the above described specially arranged superconducting cylindrically symmetric correction coils $C_1$ through $C_p$ which are arranged together with the partial coils 1a, 1b, 2a, and 2b of the main field coil in the helium chamber 23. In principle the correction coils $C_1$ through $C_p$ can also be fed from a power supply. It is preferred when the correction coils, however, exhibit a superconducting switch and are driven in the "persistent mode" e.g. short-circuited.

Two of the p correction coils $C_1$ through $C_p$ are located in both halves of the cryostat.

We claim:

1. A superconducting magnetic resonance imaging apparatus having a homogeneous magnetic field directed along a z-coordinate axis and having a center at an origin of the z-coordinate axis, the apparatus comprising:

a pair of mutually similar outer coils coaxial with the z-axis at a first axial separation $g_1$ from each other and symmetric with respect to a middle plane perpendicular to the z-axis, the first axial separation being between ¼ and ¾ of an outer coil inner diameter, the outer coils having a first current flowing in a first current direction;

a pair of mutually similar inner coils, having an inner coil width b, coaxial with the outer coils at a second axial separation $g_2$ from each other and symmetric with respect to the middle plane, the second axial separation being within 15% of the first axial separation, the inner coils having a second current flowing in a second current direction opposite the first current direction;

a cryostat containing the outer and inner field coils and having an axial room temperature bore extending along the z-axis and having a transverse access opening transverse to the z-axis;

ferromagnetic homogeneity means, located at selected positions on a surface of the room temperature bore on both sides of the transverse access opening, the positions being selected to compensate at least one component of a tesseral field distortion of a type $A_{nm}$ with n=1 through 6 and m=1 through n; and at least one or more superconducting correction coils, each correction coil having separate current terminals and being coaxial with the outer and inner field coils, each correction coil comprising a first partial coil having a first partial current flowing in a first partial current direction and a second partial coil having a second partial current flowing in a second partial current direction opposite the first partial current direction, wherein the first and second partial coils are coaxial with the z-axis and have a first partial diameter and a second partial diameter which are less than the outer coil inner diameter, wherein the first partial coils are located at an axial distance $z_1$ from the center, with $g_2/2 \geq |z_1| \geq g_2/2+b$ and the second partial coils are located at an axial distance $z_2$ from the center, with $g_2/2+b<|z_2|$.

2. The apparatus of claim 1, wherein winding numbers of the correction coils are chosen to cancel mutual inductances between the inner and outer coils and the correction coils.

3. The apparatus of claim 1, wherein the first partial diameter is larger than an inner coil outer diameter.

4. The apparatus of claim 1, further comprising a third partial coil having a third partial diameter and a 4th partial coil having a fourth partial diameter, the third partial coil being closer to the middle plane than the fourth partial coil and the third partial diameter being larger than the fourth partial diameter.

5. The apparatus of claim 4, wherein the fourth partial diameter is generally equal to an inner diameter of the inner field coils.

6. The apparatus of claim 1, further comprising a first coil support for supporting the first partial coils and the inner coils and a second coil support for supporting the second partial coils and the outer coils.

7. The apparatus of claim 1, further comprising superconducting saddle coils arranged at a first separation from the z-axis generally equal to a second separation of the inner coils from the z-axis.

8. The apparatus of claim 1, wherein the ferromagnetic homogeneity mean are permanent magnets.

9. The appartus of claim 1, wherein the first and second partial diameters are generally equal.

* * * * *

UNITED STATES PATENT AND TRADEMARK OFFICE
CERTIFICATE OF CORRECTION

PATENT NO. : 5,545,997
DATED : August 13, 1995
INVENTOR(S) : Westphal, et al.

It is certified that error appears in the above-indentified patent and that said Letters Patent is hereby corrected as shown below:

Column 2, line 22, replace existing equation (3)
"$B_z = A_{00} + A_{80}z^8 + A_{10,0}z^{10} +$" with --$B_z = A_{00} + A_{80}z^8 + A_{10,0}z^{10} + \cdots$--.

Column 3, line 38, replace "$g_2/2 \geq |z| \geq g_2/2+b$" with
--$g_2/2 \leq |z| \leq g_2/2+b$--.

Column 8, line 1, replace "$g_2/2 \geq |z| \geq g_2/2+b$" with
--$g_2/2 \leq |z| \leq g_2/2+b$--.

Column 8, line 44, replace "1.8 g≥r≥2 g" with --1.8 g ≤ r ≤ 2 g--.

In Claim 1 (column 10, line 6), replace "$g_2/2 \geq |z| \geq g_2/2+b$" with
--$g_2/2 \leq |z| \leq g_2/2 + b$--.

Signed and Sealed this

Thirty-first Day of December, 1996

Attest:

BRUCE LEHMAN

Attesting Officer     Commissioner of Patents and Trademarks